(12) United States Patent
Odén et al.

(10) Patent No.: US 9,169,122 B2
(45) Date of Patent: Oct. 27, 2015

(54) MANUFACTURE OF CRYSTALLITE PARTICLES

(75) Inventors: Magnus Odén, Tullinge (SE); Emma Björk, Linköping (SE)

(73) Assignee: Nanolith Sverige AB (SE)

( * ) Notice: Subject to any disclaimer, the term of this patent is extended or adjusted under 35 U.S.C. 154(b) by 15 days.

(21) Appl. No.: 13/825,454

(22) PCT Filed: Sep. 21, 2011

(86) PCT No.: PCT/EP2011/066381
§ 371 (c)(1),
(2), (4) Date: May 31, 2013

(87) PCT Pub. No.: WO2012/038455
PCT Pub. Date: Mar. 29, 2012

(65) Prior Publication Data
US 2014/0030180 A1    Jan. 30, 2014

Related U.S. Application Data

(60) Provisional application No. 61/385,693, filed on Sep. 23, 2010.

(30) Foreign Application Priority Data

Sep. 23, 2010 (SE) ........................ 1050988

(51) Int. Cl.
| | |
|---|---|
| *C01B 33/12* | (2006.01) |
| *C01B 37/02* | (2006.01) |
| *B82Y 30/00* | (2011.01) |
| *B82Y 40/00* | (2011.01) |
| *C01B 33/187* | (2006.01) |
| *B32B 3/26* | (2006.01) |
| *B44C 1/22* | (2006.01) |
| *A61K 47/02* | (2006.01) |
| *C01B 33/18* | (2006.01) |
| *C01B 33/193* | (2006.01) |

(52) U.S. Cl.
CPC ................. *C01B 37/02* (2013.01); *A61K 47/02* (2013.01); *B32B 3/263* (2013.01); *B44C 1/227* (2013.01); *B82Y 30/00* (2013.01); *B82Y 40/00* (2013.01); *C01B 33/187* (2013.01); *C01B 33/18* (2013.01); *C01B 33/193* (2013.01); *C01P 2002/01* (2013.01); *C01P 2004/03* (2013.01); *C01P 2004/04* (2013.01); *C01P 2004/13* (2013.01); *C01P 2004/64* (2013.01); *C01P 2006/16* (2013.01); *Y10T 428/24479* (2015.01)

(58) Field of Classification Search
CPC ...... C01B 33/18; C01B 33/187; C01B 33/193
USPC .......................................... 423/335, 338, 339
See application file for complete search history.

(56) References Cited

U.S. PATENT DOCUMENTS

| 4,973,563 A | 11/1990 | Prigge et al. |
|---|---|---|
| 2002/0041932 A1 | 4/2002 | Ogawa |
| 2003/0012931 A1 | 1/2003 | Kuroda et al. |
| 2012/0192762 A1* | 8/2012 | Yabe et al. ............... 106/287.14 |

OTHER PUBLICATIONS

Bai et al.; Gold Nanoparticles-Mesoporous Silica Composite Used as an Enzyme Immobilization Matrix for Amperometric Glucose Biosensor Construction, Sensors and Actuators B: Chemical: International Journal Devoted to Research and Development of Physical and Chemical Transducers, Elsevier SA, Switzerland, May 16, 2007, 124:1, pp. 179-186, XP022080520.

De Witte, K. et al.; Multi-Step Loading of Titania on Mesoporous Silica: Influence of the Morphology and the Porosity on the Catalytic Degradation of Aqueous Pollutants and VOCs, Applied Catalysis B: Environmental, Elsevier, Oct. 25, 2008, 84:1-2, pp. 125-132, XP025435054.

Hu et al.; Large-Area Silica Nanotubes With Controllable Geometry on Silicon Substrates, Applied Surface Science, Elsevier, Amsterdam. NL, Jan. 1, 2009 255:6, pp. 3563-3566. XP025865643.

International Search Report and Written Opinion for Application No. PCT/EP2011/066381 dated Mar. 26, 2013.

International Search Report and Wrtitten Opinion for Application No. PCT/EP2011/066384 dated Mar. 26, 2013.

Johansson, E.M. et al: Synthesis and Characterization of Large Mesoporous Silica SBA-15 Sheets with Ordered Accessible 18 nm Pores, Materials Letters, North Holland Publishing Company, Amsterdam, NL, Oct. 15, 2009, 63:24-25, pp. 2129-2131, XP026467350.

Johansson, Emma M. et al.; The Effects on Pore Size and Particle Morphology of Heptane Additions to the Synthesis of Mesoporous Silica SBA-15, Microporous and Mesoporous Materials, Sep. 1, 2010,133:1-3, pp. 66-74, XP055014159.

Mesa M. et al.; Morphology and Porosity Characteristics Control of SBA-16 Mesoporous Silica. Effect of the Triblock Surfactant Pluronic F127 Degradation During the Synthesis. Solid State Sciences, Elsevier, Paris. FR, Aug. 1, 2005, 7:8, pp. 990-997, XP004997002.

(Continued)

*Primary Examiner* — Matthew E Hoban
*Assistant Examiner* — James Fiorito
(74) *Attorney, Agent, or Firm* — Lerner, David, Littenberg, Krumholz & Mentlik, LLP

(57) ABSTRACT

A method for the manufacture of crystallite particles, said method comprising the steps of: a) reacting a reaction solution comprising a silicate, a micelle forming agent, an alkane, a salt under stirring at pH 2 or lower, wherein the reaction solution comprises HCl in a concentration of at least 1.5 M, wherein the stirring is performed not more than 10 minutes, and b) treating the obtained material to remove the micelle forming agent with one method selected from i) heat treating the material above 300° C., ii) treating the material with at least one selected from $H_2O_2$, and $H_2SO_4$, iii) treating the material with microwaves to digest the micelle forming agent. An advantage is that the time for the synthesis is shortened considerably compared to the prior art.

8 Claims, 7 Drawing Sheets

(56) References Cited

OTHER PUBLICATIONS

Shiori Kubo et al.; Salt-Induced Formation of Uniform Fiberlike SBA-15 Mesoporous Silica Particles and Application to Toluene Adsorption, Langmuir, Nov. 1, 2007, 23:23, pp. 11761-11768, XP55014158.

Wang Y et al.; Synthesis of Length Controllable Mesoporous SBA-15 Rods, Materials Chemistry and Physics, Elsevier SA. Switzerland, Taiwan, Republic of China, Jun. 15, 2009, 115:2-3, pp. 649-655. XP026018602.

Zhao, D. et al.; High-Yield Synthesis of Periodic Mesoporous Silica Rods and Their Replication to Mesoporous Carbon Rods, Advanced Materials, Wiley VCH Verlag. DE, Dec. 3, 2002, 14:23, pp. 1742-1745, XP002418214.

U.S. Office Action for U.S. Appl. No. 13/825,472 dated Feb. 5, 2015.

Zhao, Continuous mesoporous silica films with highly ordered large pore structures, 1998, Advanced Materials, 10, 1380-1385.

* cited by examiner

MANUFACTURE OF CRYSTALLITE PARTICLES

CROSS-REFERENCE TO RELATED APPLICATIONS

The present application is a national phase entry under 35 U.S.C. §371 of International Application No. PCT/EP2011/066381 filed Sep. 21, 2011, published in English, which claims priority from U.S. Application No. 61/385,693 filed Sep. 23, 2010, and Swedish Application No. 1050988-3 filed Sep. 23, 2010 all of which are incorporated herein by reference.

TECHNICAL FIELD

The present invention relates generally to a method for the manufacture of structured particles as well as particles manufactured by the method.

BACKGROUND

Ordered mesoporous silica can be synthesized in a variety of pore sizes, pore shapes and morphologies. Due to its potential applications in e.g. separation, catalysis, adsorption and as a template, this group of materials has received much interest the last decades. Depending on the application various morphologies, pore sizes and pore shapes are preferred.

One example of mesoporous silica is SBA-15. SBA-15 with its hexagonally ordered cylindrical pores can be synthesized in a variety of morphologies e.g. fibers, spheres, platelets or monodispersed rods. Wang et al in Mater. Chem. Phys, 115(2009) 649-655 discloses SBA-15 rods with different lengths. Si-compounds are polymerized to larger structures. HCl concentrations of 2.5, 2.0, 1.0, and 0.5 M were tested and no big differences were found. In FIG. 6 of Wang et al it can be seen that a high acidity leads to shorter structures. Glycerol is stated to play an important role for the controlled formation of rods according to the teachings for instance at the end of section 3.2.

The pore size of SBA-15 is normally 6-9 nm but it can be increased by e.g. adding swelling agents such as 1,3,5-trimethylbenzene (TMB) or by varying the hydrothermal treatment time and temperature. Increasing the pore size using swelling agent is possible up to a certain limit, but due to a phase transition from ordered hexagonal pores to disordered mesocellular foams this is the maximum pore size obtained. Low temperature syntheses with alkanes and $NH_4F$ can increase the pore size where the morphology can be varied by varying synthesis parameters.

E. Johansson et al in Microporous and Mesoporous Materials, volume 133, issue 1-3, pages 66-74, September 2010 discloses manufacture of mesoporous silica in the form of crystallites with hexagonally arranged pores running through the crystallites. The crystallites are always attached to each other. The crystallites can be attached end-to-end to form fibers, or the crystallites can be attached side-by-side to form sheets. It is disclosed that heptane in the presence of $NH_4F$ works as a pore swelling agent. The HCl concentration was varied between 1.37-1.98 M.

E. Johansson et al in Materials Letters, volume 63, Issue 24, pages 2129-2131, October 2009 discloses mesoporous silica in the form of crystallites attached side-by-side to sheets, where the pores are parallel to the sheet normal.

A problem in the state of art is how to separate the crystallites so that they are suitable for further use. It is also a problem in the prior art that the time for the synthesis is rather long.

SUMMARY

It is an object of the present invention to alleviate at least some of the disadvantages of the prior art and to provide an improved method to obtain separate crystallites and shorten the time for the synthesis of the crystallites.

The inventors have performed extensive research and have unexpectedly found that an increased amount of HCl in combination with shortened stirring time during the synthesis give separated particles with the desired properties.

It was discovered that glycerol was not needed in order to obtain in the desired structures.

There is provided a method for the manufacture of particles, said method comprising the steps of: a) reacting a reaction solution comprising a silicate, a micelle forming agent, an alkane, a salt under stirring at pH 2 or lower, wherein the reaction solution comprises HCl in a concentration of at least 1.5 M, wherein the stirring is performed not more than 10 minutes, and b) treating the obtained material to remove the micelle forming agent with one method selected from i) heat treating the material above 300° C., ii) treating the material with at least one selected from $H_2O_2$, and $H_2SO_4$, and iii) treating the material with microwaves to digest the micelle forming agent.

It is an advantage that separated particles are obtained within a rather short period of time compared to the prior art. The time for the synthesis is shortened considerably.

BRIEF DESCRIPTION OF THE DRAWINGS

The invention is described with reference to the following drawings in which.

DETAILED DESCRIPTION

Figure 1:
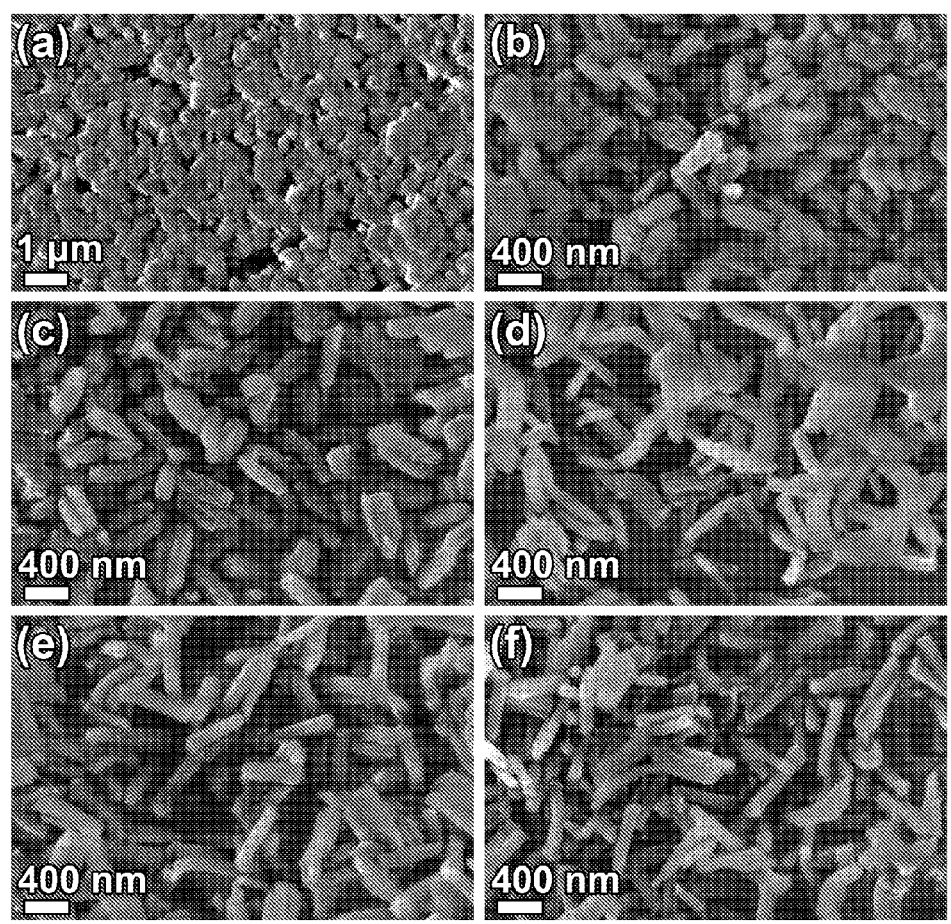
FIG. 1 shows micrographs of particles synthesized with varying HCl concentration.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used throughout the claims and the description the term calcine denotes to heat a substance to a high temperature but below the melting or fusing point. A calcinated particle is a particle heated to such a temperature.

As used throughout the claims and the description the term crystallite denotes small, often microscopic crystals that, held together through highly defective boundaries, constitute a polycrystalline solid.

As used throughout the claims and the description the term mesoporous material denotes a material containing pores with diameters between 2 and 50 nm.

In a first aspect there is provided a method for the manufacture of particles, said method comprising the steps of: a) reacting a reaction solution comprising a silicate, a micelle forming agent, an alkane, a salt under stirring at pH 2 or lower, wherein the reaction solution comprises HCl in a concentration of at least 1.5 M, wherein the stirring is performed not more than 10 minutes, and b) treating the obtained material to remove the micelle forming agent with one method selected from i) heat treating the material above 300° C., ii) treating the material with at least one selected from $H_2O_2$, and $H_2SO_4$, and iii) treating the material with microwaves to digest the micelle forming agent.

In an alternative embodiment the pH is 1.5 or lower. In another embodiment the pH is 1 or lower.

The inventors have unexpectedly found that if a pH of 2 or lower, preferably 1 or lower is used it is possible to manufacture separated particles, which in turn can be used for other applications. One example of such an application includes but is not limited to a surface wherein the separated mesoporous silica particles are adsorbed to the surface.

In one embodiment the reaction solution comprises HCl in concentration above 1.4 M. In an alternative embodiment the reaction solution comprises HCl in concentration from 1.4 to 2.5 M. In an alternative embodiment the reaction solution comprises HCl in concentration of at least 2.0 M. In one embodiment the reaction solution comprises HCl in concentration above 1.4 M. In one embodiment the reaction solution comprises HCl in concentration above 1.5 M. In one embodiment the reaction solution comprises HCl in concentration above 1.6 M. In another embodiment the reaction solution comprises HCl in concentration above 1.7 M. In another embodiment the reaction solution comprises HCl in concentration above 1.63 M. In one embodiment the reaction solution comprises HCl in concentration from 1.6 to 2.0 M. In one embodiment the reaction solution comprises HCl in concentration from 1.7 to 2.0 M. In one embodiment the reaction solution comprises HCl in a concentration below 2.5 M. In one embodiment the reaction solution comprises HCl in a concentration below 2.0 M.

In one embodiment the stirring is performed not more than 10 minutes. In another embodiment the stirring is performed not more than 5 minutes. In an alternative embodiment the stirring is performed not more than 4 minutes. In yet an alternative embodiment the stirring is performed not more than 3 minutes.

It has been discovered that the combination of a HCl concentration as described above and the stirring time of not more than 10 minutes, preferably not more than 5 minutes, more preferably not more than 4 minutes give separated particles and shortens the time for the synthesis.

In one embodiment the silicate is at least one silicate selected from the group consisting of tetramethyl orthosilicate, tetraethyl orthosilicate, tetrapropyl orthosilicate, tetrabutyl orthosilicate, and sodium silicate. In an alternative embodiment the silicate is at least one silicate selected from the group consisting of tetraethyl orthosilicate, tetrapropyl orthosilicate, tetrabutyl orthosilicate, and sodium silicate. In one embodiment the silicate is tetraethyl orthosilicate. In one embodiment one silicate selected from the above silicates is used. In an alternative embodiment a mixture of more than one silicate is used.

In one embodiment the micelle forming agent is a triblock copolymer. In one embodiment the micelle forming agent is an ethylene oxide/propylene oxide/ethylene oxide (EO PO EO) triblock copolymer. In one embodiment the micelle forming agent is an $EO_{20}PO_{70}EO_{20}$ triblock copolymer.

In one embodiment the alkane is at least one selected from the group consisting of pentane, hexane, heptane, octane, nonane, decane, undecane, and dodecane. In one embodiment the alkane is heptane.

In one embodiment the salt is at least one selected from the group consisting of $NH_4F$, KCl, and $NaSO_4$. In one embodiment the salt is $NH_4F$.

In one embodiment the method further comprises the step of utilizing the particles in a process for the manufacture of at least one device selected from the group consisting of a battery, a catalyst, a mesoreactor, a solar cell, and a sensor. In one embodiment the particles are used during a phase of the manufacturing process and are then removed. An example of removal includes but is not limited to removal by etching. In embodiments where the particles are removed the particles are not present in the final product, but have been used to obtain a desired structure. In one embodiment the method further comprises the step of utilizing the particles in a process for the manufacture of a drug carrier.

In a second aspect there is provided a particle manufactured with the method described above.

In one embodiment the particles are rodlike with pores running along the long axis of the particles. In one embodiment the pores are through pores.

In one embodiment the diameter of the pores is from 10 to 20 nm. In another embodiment the diameter of the pores is from 8 to 22 nm. In an alternative embodiment the diameter of the pores is from 12 to 20nm. In an alternative embodiment the diameter of the pores is from 12 to 18 nm. In another embodiment the diameter of the pores is from 13 to 18 nm. In an alternative embodiment the diameter of the pores is from 13 to 16 nm. In another embodiment the diameter of the pores is about 18 nm. It must be realized that the pores do not necessarily have perfect circular cross sections due to the manufacturing process. For non-circular cross sections the diameter of the pores is the maximum distance between any two points on the circumference of a perpendicular cross section. The diameter is the largest possible dimension of a perpendicular cross section.

EXAMPLES

Monodispersed SBA-15 rods were synthesized in the presence of heptane and $NH_4F$ in a low temperature synthesis.

The length of the rods can be varied by changing the HCl concentration. Further the rods or particles were separated using a particular HCl concentration corresponding to a particular pH. Furthermore the pore size can be tuned by changing the hydrothermal treatment time and temperature.

Synthesis

Hydrochloric acid (purity≥37%, puriss. p.a., Fluka, ACS Reagent, fuming), triblock copolymer $EO_{20}PO_{70}EO_{20}$ (P123) (Aldrich), ammonium fluoride (purity≥98.0%, puriss. p.a., ACS reagent, Fluka), tetraethyl orthosilicate (TEOS) (reagent grade, 98%, Aldrich) and heptane (99%, Reagent-Plus®, Sigma-Aldrich) were used as received.

In a typical synthesis 2.4 g of P123 and 0.028 g of $NH_4F$ was dissolved in 80 ml HCl solution. The HCl concentration in the solution was varied between 1.37-1.98 M. The pH of the solution was thereby varied between 0.8 and 0.9. The mixture was stirred at 20° C. until the polymer was dissolved. Heptane or decane respectively with an alkane to P123 molar ratio of 280 was premixed with 5.5 ml TEOS and then added to the micellar solution. The synthesis was kept under vigorous stirring for 4 min and then under static conditions for 5 min-3 h. After the reaction the solution was transferred to a teflon-flask for hydrothermal treatment at 80-130° C. for 6-120 h. The material was then filtered and washed with distilled water and dried in 100° C. over night. Finally, the material was calcinated in 550° C. for 5 h with a temperature ramp of 10° C./min.

Parameters such as heptane and TEOS concentrations were varied. In these syntheses the HCl concentration was fixed to 1.83 M and the heptane to P123 molar ratio was varied between 16 and 380 with a fixed TEOS to P123 molar ratio of 60. Furthermore, the TEOS to P123 molar ratio was varied between 45 and 90 with a fixed heptane to P123 molar ratio at 280.

Characterization

Scanning electron microscopy (SEM) was performed with a Leo 1550 Gemini Scanning Electron Microscope operated at 3 kV and a working distance of 3-5 mm.

Nitrogen sorption isotherms were obtained with a Micromeritics ASAP 2020 at 77 K with samples degassed at 573 K for 9 h. Pore size distribution was calculated from the adsorption isotherm using the KJS-method and the BET-surface area from the relative pressure of 0.06-0.17. The total pore volume was estimated at PO/P=0.975. Transmission electron microscopy (TEM) was performed with a FEI Tecnai G2 TF 20 UT microscope operated at 200 kV.

Samples were prepared by dispersing the sample in acetone and depositing it on a hollow carbon grid.

Results

As seen in the SEM micrographs, FIG. 1, the particle shape varies with HCl concentration. In FIG. 1(*a*) the particles are agglomerated and ~0.4 pm wide and equally long. Increasing the HCl concentration to 1.68-1.73 M or above, the particles become separated and have a spindle shape with a length of ~400 nm and a width of 150-200 nm. Further increase of the HCl concentration elongates the spindle like particles to ~600 nm, FIG. 1(*d*). A higher HCl concentration yields 500-700 nm long and 100 nm wide rodlike particles, see FIG. 1 (*e*) and (*f*).

Figure 2:
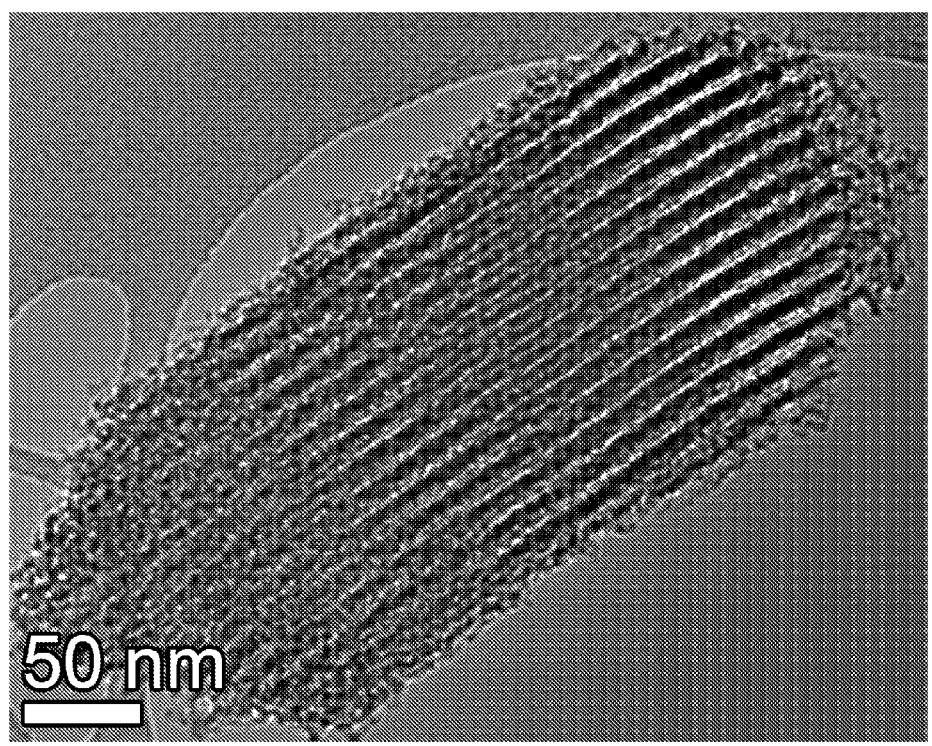
FIG. 2 shows a TEM micrograph of a spindle particle.

FIG. 2 shows that the pores are running along the long axis of the particles and are arranged in a hexagonal order.

Figure 3:
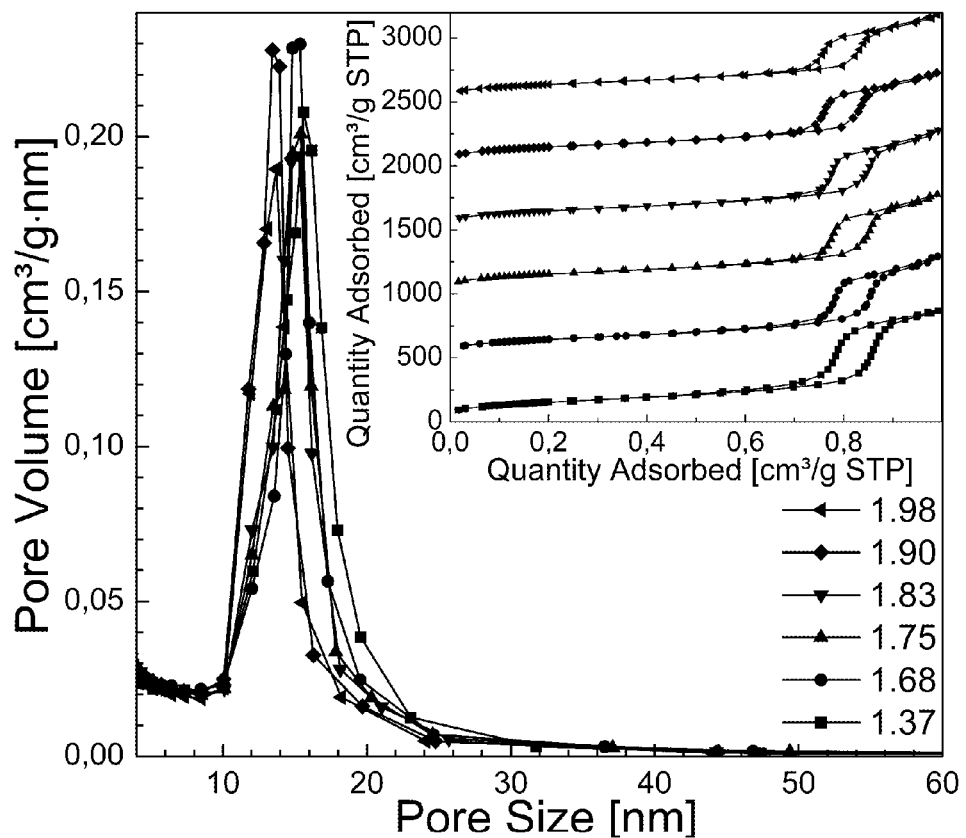
FIG. 3 shows pore size distributions (a) and physisorption isotherms (b) calculated with the KJS-method for samples synthesized with varying HCl concentration and hydrothermal treatment in 100° C. for 24 h.

The physisorption isotherms for all morphologies, FIG. 3, are all type IV isotherms with type 1 hysteresis loops. These isotherms are typical for SBA-15 with its cylindrical, hexagonally ordered pores. The pore size distributions for the materials calcinated at 100° C. for 24 h are narrow and reveal a pore size of 11-17 nm. All physisorption data are included in Table I.

TABLE I

Synthesis conditions and physisorption data for the synthesized materials.

| Sample | HCl [mol/l] | TEOS/P123 molar ratio | Heptane/P123 molar ratio] | Ageing temp. [° C.] | Ageing time [h] | Static time [h] | Surface area [m²/g] | Pore size (diameter) [nm] | Total pore volume [cm³/g] |
|---|---|---|---|---|---|---|---|---|---|
| A | 1.37 | 60 | 280 | 100 | 24 | 3 | 560 | 15.6 | 1.34 |
| B | 1.68 | 60 | 280 | 100 | 24 | 3 | 525 | 15.1 | 1.22 |
| C | 1.75 | 60 | 280 | 100 | 24 | 3 | 559 | 15.4 | 1.20 |
| D | 1.83 | 60 | 280 | 100 | 24 | 3 | 542 | 15.1 | 1.20 |
| E | 1.90 | 60 | 280 | 100 | 24 | 3 | 538 | 13.7 | 1.13 |
| F | 1.98 | 60 | 280 | 100 | 24 | 3 | 498 | 13.7 | 1.05 |
| t6 | 1.75 | 60 | 280 | 100 | 6 | 3 | 862 | 11.8 | 0.82 |
| t120 | 1.75 | 60 | 280 | 100 | 120 | 3 | 438 | 15.8 | 1.12 |
| T80 | 1.75 | 60 | 280 | 80 | 24 | 3 | 778 | 13.1 | 1.31 |
| T130 | 1.75 | 60 | 280 | 130 | 24 | 3 | 513 | 16.1 | 1.21 |
| T130-t120 | 1.75 | 60 | 280 | 130 | 120 | 3 | 410 | 16.8 | 1.27 |
| Stat5 | 1.75 | 60 | 280 | 100 | 24 | 5 min | 562 | 17.1 | 1.40 |
| Decane | 1.75 | 60 | 280 | 100 | 24 | 3 | 615 | 13.3 | 1.16 |
| 45 TEOS | 1.83 | 45 | 280 | 100 | 24 | 1 | 629 | ~9-13 | 1.74 |
| 75 TEOS | 1.83 | 75 | 280 | 100 | 24 | 1 | 692 | 12.4 | 1.06 |
| 16 hep | 1.83 | 60 | 16 | 100 | 24 | 1 | 603 | 11.5 | 1.03 |
| 50 hep | 1.83 | 60 | 50 | 100 | 24 | 1 | 545 | 12.8 | 1.08 |
| 100 hep | 1.83 | 60 | 100 | 100 | 24 | 1 | 523 | 12.9 | 1.06 |
| 200 hep | 1.83 | 60 | 200 | 100 | 24 | 1 | 503 | 13.8 | 1.09 |
| 400 hep | 1.83 | 60 | 400 | 100 | 24 | 1 | 500 | 14.3 | 1.12 |

The synthesis of SBA-15 rods was performed by varying the stirring time and HCl concentration. The separation of particles was only possible at higher concentrations of HCl even when the stirring time was decreased to 5 min. The size and shape of the particles synthesized with the lowest HCl concentration are identical to the size and shape of the crystallites building up the morphologies for this system. During the particle growth and polymerization of TEOS, the hydroxyl group density is decreased leading to more passive surfaces that cannot attach to each other. The passivation is higher on the mantle surface of the particles compared to the ends since the hydroxyl groups on located at the ends are more shielded from the acid by the micelles. This is seen as one of the sources for the end-to-end attachments of particles.

During the early formation of the hexagonal structure in SBA-15, cylindrical micelles or groups of them attach together, side to side, due to the hydroxyl groups. Hence, when the lower HCl concentration is used, the particles can grow wider compared to when more HCl is present.

As seen in FIG. 1, the particle length is increasing with the HCl concentration. This is in opposite to a previous study by Wang et al. cited above who used glycerol to straighten the particles, a decreased stirring time to separate them and a variation of HCl concentration between 0.5-2.5 M. In that study it was stated that variation in particle length was due to a combination of that high concentrations of acid yield a larger number of seeds from which particles can be formed, the increased passivation of the basal planes and that TEOS in combination with glycerol form bridged silane species.

Figure 4:
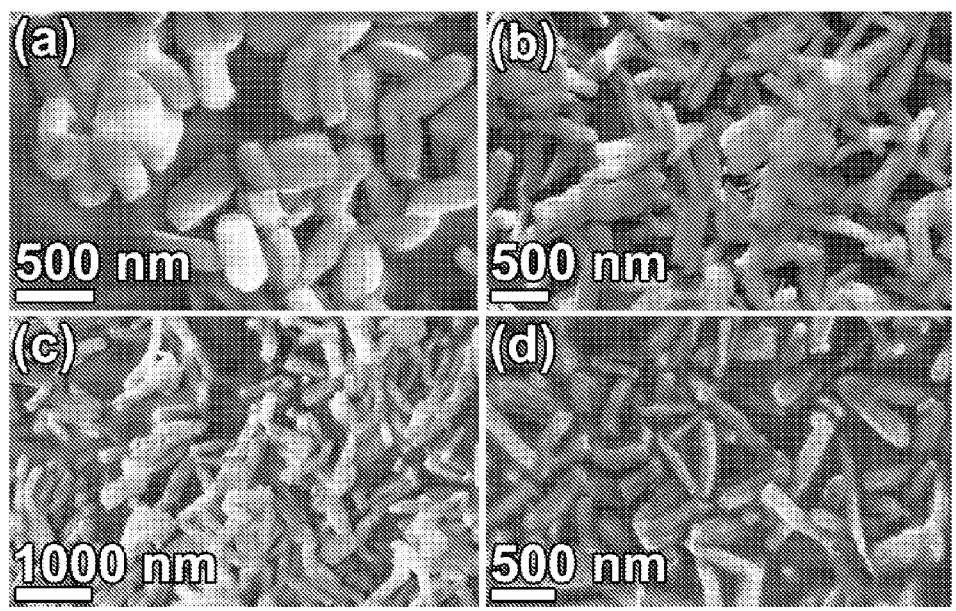
FIG. 4 shows SEM micrographs of particles synthesized with varying heptane concentration; (a) 16, (b) 50, (c) 200 and (d) 400 in heptane/P123 molar ratio.
Figure 5:
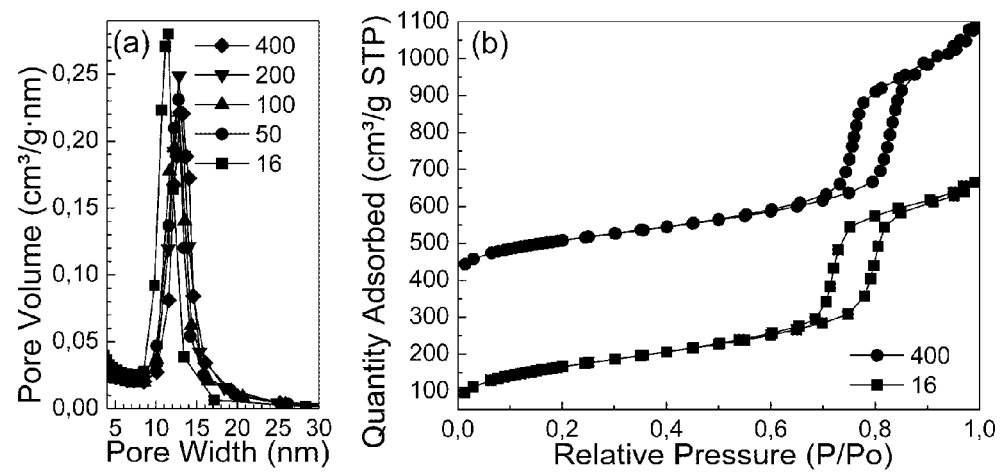
FIG. 5 shows pore size distributions (a) and physisorption isotherms (b) calculated with the KJS-method for rods synthesized with varying heptane to P123 molar ratio.

For a fixed HCl concentration of 1.83 M, the material can be further altered by variations in the heptane concentration (heptane to P123 molar ratio), see FIGS. 4 and 5. As seen in FIG. 4 the length of the particles are increasing with increasing heptane to P123 molar ratio. The pore size is increasing with increasing the heptane concentration, see FIG. 5.

Figure 6:
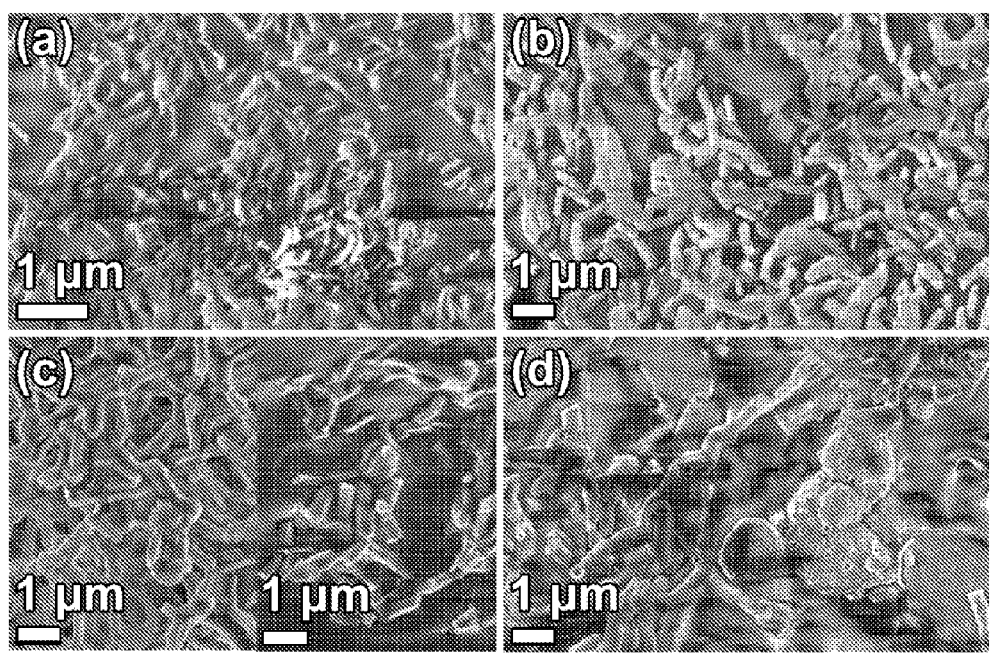
FIG. 6 shows SEM micrographs of particles synthesized with varying TEOS concentration; (a) 45, (b) 75, (c) 90 and (d) 105 in TEOS/P123 molar ratio.
Figure 7:
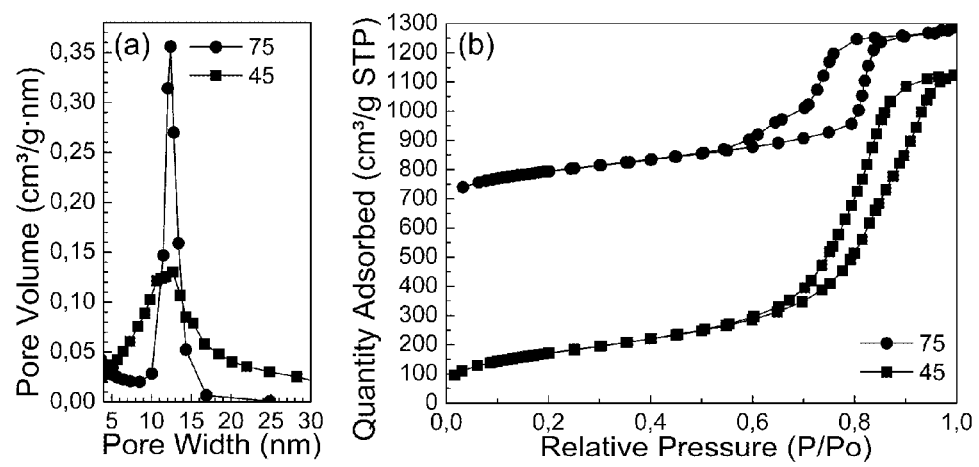
FIG. 7 shows pore size distributions (a) and physisorption isotherms (b) calculated with the KJS-method for rods synthesized with varying heptane to P123 molar ratio.

Furthermore, rods can be synthesized with various amounts of TEOS, see FIGS. 6 and 7. The rods are though gluing together with increasing amounts of TEOS, and the physisorption data, FIG. 7, reveals that there is a mixture of pore structures for TEOS to P123 molar ratios ≤75.

The invention claimed is:

1. A method for the manufacture of crystallite particles, said method comprising the steps of:
   a) reacting a reaction solution comprising a silicate, a micelle forming agent, an alkane, and a salt with HCl under stirring at pH 2 or lower, wherein the reaction solution comprises the HCl in a concentration of at least 1.4 M, wherein the reacting takes place at 20° C.; and wherein the stirring is performed for not more than 5 minutes; and
   b) treating the material obtained in step a to remove the micelle forming agent with a method selected from the group consisting of
      i) heat treating the material above 300° C.,
      ii) treating the material with at least one compound selected from the group consisting of $H_2O_2$ and $H_2SO_4$, and
      iii) treating the material with microwaves to digest the micelle forming agent; and
   wherein the manufactured crystallite particles are separate from each other.

2. The method according to claim 1, wherein the reaction solution comprises the HCl in a concentration of at least 2.0 M.

3. The method according to claim 1, wherein the silicate is at least one silicate selected from the group consisting of tetramethyl orthosilicate, tetraethyl orthosilicate, tetrapropyl orthosilicate, tetrabutyl orthosilicate, and sodium silicate.

4. The method according to claim 1, wherein the micelle forming agent is a triblock copolymer.

5. The method according to claim 1, wherein the alkane is at least one alkane selected from the group consisting of pentane, hexane, heptane, octane, nonane, decane, undecane, and dodecane.

6. The method according to claim 1, wherein the alkane is heptane.

7. The method according to claim 1, wherein the salt is at least one salt selected from the group consisting of $NH_4F$, KCl, and $NaSO_4$.

8. The method according to claim 1, wherein the crystallite particles are rodlike with pores running along the long axis of the particles.

* * * * *